(12) United States Patent
Shimokita et al.

(10) Patent No.: US 11,313,788 B2
(45) Date of Patent: Apr. 26, 2022

(54) BODY FLUID ANALYSIS DEVICE

(71) Applicant: GENIAL LIGHT CO., LTD., Hamamatsu (JP)

(72) Inventors: Ryo Shimokita, Hamamatsu (JP); Takashi Sawada, Toyohashi (JP); Tatsuyuki Fujita, Hamamatsu (JP)

(73) Assignee: GENIAL LIGHT CO., LTD., Hamamatsu (JP)

( * ) Notice: Subject to any disclaimer, the term of this patent is extended or adjusted under 35 U.S.C. 154(b) by 0 days.

(21) Appl. No.: 16/979,961

(22) PCT Filed: Jun. 5, 2019

(86) PCT No.: PCT/JP2019/022305
§ 371 (c)(1),
(2) Date: Sep. 11, 2020

(87) PCT Pub. No.: WO2019/239980
PCT Pub. Date: Dec. 19, 2019

(65) Prior Publication Data
US 2021/0048385 A1    Feb. 18, 2021

(30) Foreign Application Priority Data

Jun. 15, 2018   (JP) .............................. JP2018-114397

(51) Int. Cl.
*G01N 21/27* (2006.01)
*G01N 33/493* (2006.01)
*G01N 33/72* (2006.01)

(52) U.S. Cl.
CPC ........... *G01N 21/27* (2013.01); *G01N 33/493* (2013.01); *G01N 33/72* (2013.01)

(58) Field of Classification Search
CPC ...... G01N 21/27; G01N 33/493; G01N 33/72; A61B 5/1455
See application file for complete search history.

(56) References Cited

U.S. PATENT DOCUMENTS

2008/0144005 A1   6/2008   Guiney et al.
2008/0297769 A1   12/2008  Bamberg et al.
(Continued)

FOREIGN PATENT DOCUMENTS

JP   S57500305 A   2/1982
JP   S62000838 A   1/1987
(Continued)

OTHER PUBLICATIONS

M. Pluta, "Optoelectronic device for hematocrit measurements", 2015,Photonics Applications in Astronomy, Communications, Industry, and High-Energy Physics Experiments (Year: 2015).*

(Continued)

*Primary Examiner* — Maurice C Smith
(74) *Attorney, Agent, or Firm* — Alleman Hall Creasman & Tuttle LLP (57) ABSTRACT

A body fluid analysis device includes a light source, a detector, a normalization part, and a calculation part. The light source is configured to emit light at a first wavelength and light at a second wavelength different from each other to a body fluid. The detector is configured to receive light emitted from the light source and transmitted through the body fluid or light reflected by the body fluid, and is configured to detect intensity of the light. The normalization part is configured to calculate a ratio of an intensity of light emitted at the second wavelength to an intensity of light emitted at the first wavelength, both of which are detected by the detector. The calculation part is configured to calculate a concentration of a predetermined component included in the body fluid on the basis of the ratio calculated by the normalization part.

8 Claims, 5 Drawing Sheets

(56) References Cited

U.S. PATENT DOCUMENTS

2014/0024904 A1* 1/2014 Takinami ............... A61B 5/489
                                                              600/316
2019/0195802 A1* 6/2019 Attar ..................... G01J 3/2803

FOREIGN PATENT DOCUMENTS

| JP | S62052434 A | 3/1987 |
| JP | H06241981 A | 9/1994 |
| JP | 2002156376 A | 5/2002 |
| JP | 2017506342 A | 3/2017 |
| WO | 8102633 A1 | 9/1981 |
| WO | 2013147200 A1 | 10/2013 |

OTHER PUBLICATIONS

ISA Japan Patent Office, International Search Report Issued in International Application No. PCT/JP2019/022305, dated Sep. 3, 2019, WIPO, 8 pages.

* cited by examiner

BODY FLUID ANALYSIS DEVICE

TECHNICAL FIELD

The present invention relates to a body fluid analysis device configured to irradiate a body fluid with light so as to analyze the body fluid on the basis of light transmitted through the body fluid.

BACKGROUND ART

A catheter is placed in a bladder, and urine led from inside the bladder is stored in a urine bag in some cases with respect to, for example, a patient subjected to surgery under general anesthesia or a patient who cannot move away from a bed over a long term. The urine bag includes a urine introduction tube coupled to an outer end portion of the catheter, a storage part coupled to the introduction tube and configured to store urine, and a discharge tube configured to discharge outside a certain amount of the urine stored in the storage part (refer to Patent Document 1).

Meanwhile, if the catheter is left in the bladder, inflammation due to bacterial infection or the like may occur in the bladder and a kidney connected thereto particularly for a patient whose immune strength is lowered. Therefore, in order to check whether the kidney is functioning normally, an amount of urine and a degree of occult blood in the urine are checked by a nurse.

Particularly in terms of the degree of occult blood in the urine, the nurse needs to visually compare a color of the urine with six stage color samples, and needs to determine whether a result of the comparison shows no need for treatment, or the color of the urine shows a need for treatment by the nurse or medical treatment by a doctor.

However, there is a possibility that hemolysis of blood in the urine may occur. If so, the color of the urine changes depending on a degree of hemolysis even if the degree of occult blood in the urine is the same. Hence, there remains the problem that the degree of occult blood cannot be determined accurately by visual observation.

PRIOR ART DOCUMENT

Patent Document

Patent Document 1: Japanese Unexamined Patent Publication No. 2002-156376

SUMMARY OF THE INVENTION

Problems to be Solved by the Invention

The present invention has been made in view of the above problem, and has for its main object to provide a body fluid analysis device capable of accurately measuring the degree of occult blood even in the presence of hemolysis in a body fluid, such as urine.

Means of Solving the Problems

Specifically, a body fluid analysis device in the present invention includes a light source, a detector, a normalization part, and a calculation part. The light source is configured to emit light at a first wavelength and light at a second wavelength different from each other to irradiate a body fluid. The detector is configured to receive the light emitted from the light source and transmitted through the body fluid or reflected by the body fluid, and is configured to detect an intensity of the light. The normalization part is configured to calculate a ratio of an intensity of the light at the second wavelength to an intensity of the light at the first wavelength, both of which are detected by the detector. The calculation part is configured to calculate a concentration of a predetermined component included in the body fluid on the basis of the ratio calculated by the normalization part.

With the body fluid analysis device, the concentration of the predetermined component included in the body fluid is calculated on the basis of the ratio of the intensity of the light at the second wavelength to the intensity of the light at the first wavelength. It is therefore possible to accurately measure a degree of occult blood even in the presence of hemolysis.

In a specific embodiment of the present invention, the body fluid is urine, and the predetermined component is hemoglobin or blood cells included in blood.

The calculation part may be configured to calculate a hematocrit value from a calculated concentration of hemoglobin.

More specifically, the first wavelength is preferably not less than 600 nm nor more than 1350 nm, and the second wavelength is preferably not less than 300 nm nor more than 600 nm.

Alternatively, a body fluid analysis device may include a light source, a detector, a normalization part, and a calculation part. The light source is configured to emit light at a third wavelength and light at a fourth wavelength different from each other to the body fluid. The detector is configured to receive light emitted from the light source and transmitted through the body fluid or reflected by the body fluid, and is configured to detect an intensity of the light. The normalization part is configured to calculate a ratio of an intensity of the light at the fourth wavelength to an intensity of the light at the third wavelength, both of which are detected by the detector. The calculation part is configured to calculate a degree of hemolysis in the body fluid on the basis of the ratio of the intensity of the light at the fourth wavelength to the intensity of the light at the third wavelength calculated by the normalization part. With the body fluid analysis device, it is possible to calculate the degree of hemolysis in the body fluid.

More specifically, the third wavelength and the fourth wavelength are preferably not less than 600 nm nor more than 1350 nm.

Effects of the Invention

With the present invention, the content ratio of the predetermined component included in the body fluid is calculated on the basis of the ratio of the intensity of the light at the second wavelength to the intensity of the light at the first wavelength. It is therefore possible to accurately measure the degree of occult blood in the body fluid even in the presence of hemolysis.

Also, with the present invention, the degree of hemolysis in the body fluid can be calculated by detecting the intensity of the light at the third wavelength and the intensity of the light at the fourth wavelength, and by calculating a ratio of the intensity of the light at the fourth wavelength to the intensity of the light at the third wavelength.

DESCRIPTION OF REFERENCE CHARACTERS 100 body fluid analysis device
1 light source
2 detector
3 information processing circuit
31 normalization part
32 calculation part

MODE FOR CARRYING OUT THE INVENTION

An embodiment of the present invention is described below with reference to the drawings.

A body fluid analysis device 100 in the embodiment is intended to analyze, for example, a state of urine passing through a urinary catheter T coupled to an end portion of a catheter retained in a bladder of an inpatient, which is extended out of a body of the inpatient. The urinary catheter T is a cylindrical tube composed of, for example, a transparent resin having light transmission properties.

The body fluid analysis device 100 is attached to the urinary catheter T and passed through the urinary catheter T in the embodiment. The body fluid analysis device 100 is configured to irradiate the urine retained in the urinary catheter T with light and then automatically carry out a real-time analysis of a degree of occult blood on the basis of transmitted light or reflected light. The body fluid analysis device 100 is described in more detail below.

Figure 1:
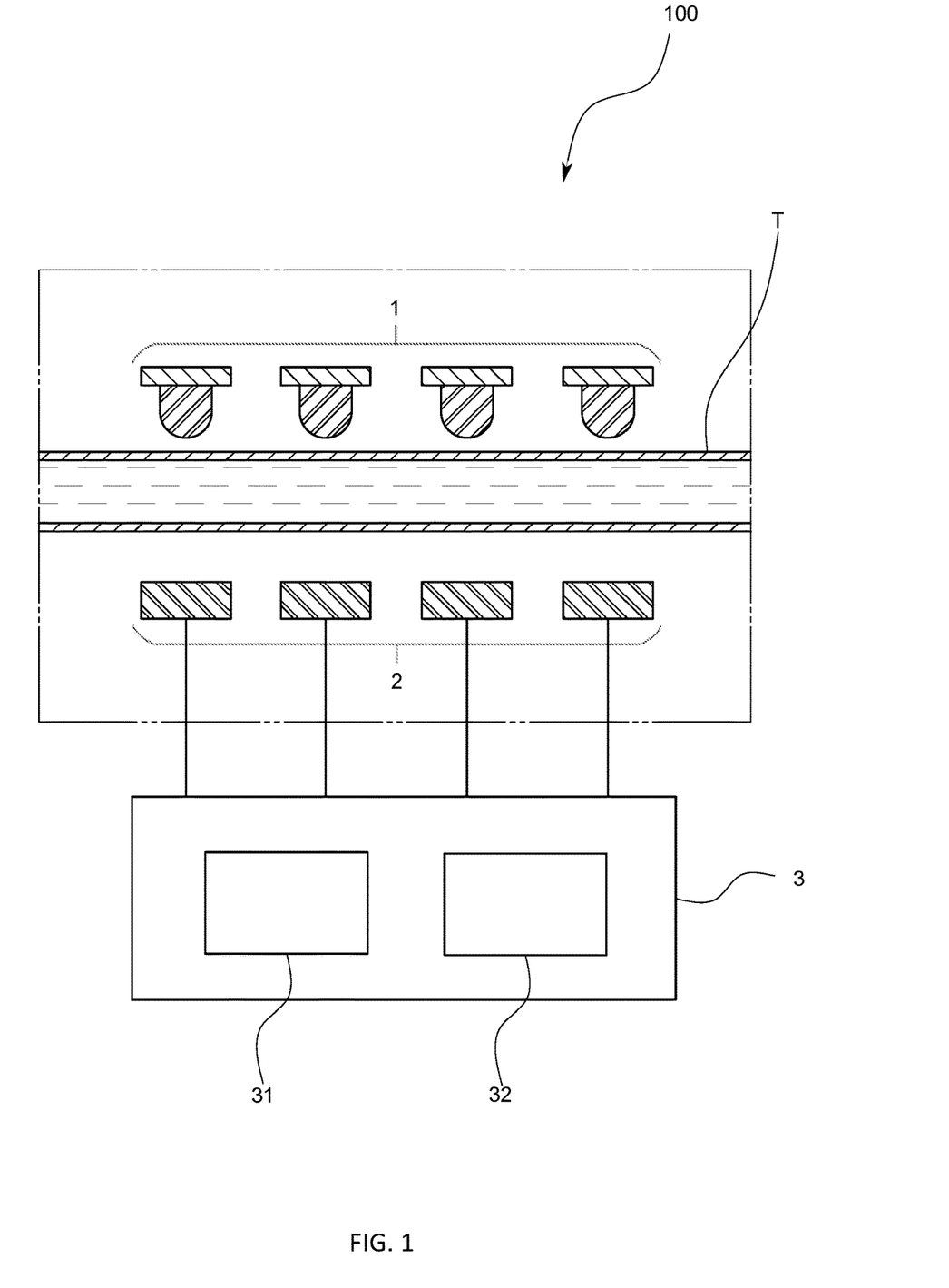
FIG. 1 is a schematic diagram of a body fluid analysis device according to an embodiment of the present invention.

The body fluid analysis device 100 includes a light source 1, a detector 2 and an information processing circuit 3, as illustrated in FIG. 1. The light source 1 emits light to urine inside the urinary catheter T. The detector 2 detects a light intensity thereof by receiving transmitted light that is emitted from the light source 1 and then passed through the urine inside the urinary catheter T, or reflected light that is emitted from the light source 1 and then reflected by the urine inside the urinary catheter T. The information processing circuit 3 measures, for example, a degree of occult blood in a body fluid on the basis of the light intensity outputted from the detector 2.

The light source 1 includes, for example, a plurality of light emitting elements. These light emitting elements are, for example, chip LEDs of single wavelength. Each of these LEDs emits a first wavelength, for example, around 650 nm and a second wavelength, for example, around 550 nm to the urine inside the urinary catheter T.

The detector 2 is, for example, a plurality of photo diodes, which are individually arranged on optical axes of these LEDs so as to oppose to, for example, the plurality of LEDs by interposing the tube therebetween.

These detectors 2 are subjected to wavelength band setting for light receivable according to a wavelength of light emitted from each of the LEDs disposed oppositely to these detectors 2.

Functions of the information processing circuit 3 can be implemented by a so-called computer including, for example, a central processing unit (CPU), memory, an analog-digital/digital-analog (AD/DA) converter, an input means, a communication means and a display device. The information processing circuit 3 performs functions as a normalization part 31 and a calculation part 32 described later by execution of an analysis program stored in the memory and by cooperation between various units.

The body fluid analysis device 100 further includes the normalization part 31 to calculate a ratio of an intensity of the light at the second wavelength to an intensity of the light at the first wavelength, and the calculation 32 to calculate a concentration of a predetermined component on the basis of the ratio.

The normalization part 31 is configured to calculate (normalize) the ratio of the intensity of the light emitted at the second wavelength to the intensity of the light emitted at the first wavelength by assuming that the intensity of the light emitted at the first wavelength is, for example, 1.

The calculation part 32 is configured to calculate, for example, a concentration of hemoglobin that is a predetermined component included in the urine, on the basis of the ratio calculated by the normalization part 31.

The following is a method for calculating a concentration of a predetermined component included in a body fluid, such as urine, by using the body fluid analysis device configured as described above.

The first step is to emit light at the first wavelength and at the second wavelength from the light source 1 to irradiate urine passing through the urinary catheter T or staying inside the urinary catheter T. The detector 2 detects the intensity of the light at the individual wavelengths after transmission through the urine.

Subsequently, the normalization part 31 calculates the ratio of the intensity of the light at the second wavelength to the intensity of the light at the first wavelength by the above method.

Thereafter, the calculation part 32 calculates a hemoglobin concentration (mg/dL) included in the urine on the basis of a calibration curve and a table previously created using urine having, for example, a known amount of blood included and a known hematocrit value and a known hemoglobin concentration.

With the body fluid analysis device 100 thus configured and the body fluid analysis method, the ratio of the intensity of the light at the second wavelength around 550 nm to the intensity of the light at the first wavelength around 650 nm, which are already detected by the detector 2. It is therefore possible to accurately calculate the concentration of hemoglobin included in the urine regardless of the presence or absence of hemolysis.

This leads to an accurate analysis of the degree of occult blood in the urine.

The present invention is not limited to the above embodiment.

The calculation part 32 may be configured to calculate a hematocrit value on the basis of the calculated hemoglobin concentration. In this case, the predetermined component may denote blood cells, and the concentration may denote a volume ratio (%) of the blood cells.

The degree of occult blood in urine may be the hemoglobin concentration or the hematocrit value thus obtained, or alternatively may be, for example, a concentration of blood in urine which is converted from the concentration of hemoglobin and blood cells.

A wavelength of light emitted from the light source 1 is not limited to that described in the above embodiment. The first wavelength may be free of influence from an absorption wavelength band (520-590 nm) and an absorption wavelength (1450 nm) of $H_2O$ that is a solvent. Specifically, the first wavelength may be a wavelength of not less than 600 nm nor more than 1350 nm, more preferably not less than 600 nm nor more than 1000 nm. The second wavelength may be a wavelength of not less than 300 nm nor more than 600 nm, more preferably not less than 500 nm nor more than 600 nm.

Light may be emitted at a plurality of wavelengths simultaneously from a plurality of light sources to the body fluid held in the tube. As such, light emitted at different wavelengths may be applied in sequence along a flow of the body fluid flowing through the tube.

The light source 1 is not limited to the LEDs. For example, a tungsten lamp that makes it possible to emit light at a plurality of wavelengths by a single light source may be used such that light at specific wavelengths, such as the first wavelength and the second wavelength, irradiates the body fluid inside the urinary catheter T by using a filter, a prism, or the like.

The detector 2 is not limited to the plurality of detectors disposed for each of the wavelengths. For example, a single detector capable of receiving light at a wide wavelength may be configured to detect light at a plurality of wavelengths in sequence. In the case of using a light source capable of emitting light at a wide range of wavelengths, such as the tungsten lamp described above, a filter or the like may be disposed on a side of the detector instead of a side of the light source so that the single detector can detect a plurality of wavelengths.

The light source 1 may further emit light at a third wavelength and light at a fourth wavelength being different from each other to irradiate the body fluid so as to obtain a degree of hemolysis in the body fluid.

In this case, the normalization part 31 calculates a ratio of an intensity of the light at the fourth wavelength to an intensity of the light at the third wavelength, both of which are detected by the detector, and the calculation part 32 calculates a degree of hemolysis on the basis of the ratio of the intensity of the light at the fourth wavelength to the intensity of the light at the third wavelength.

More specifically, the third wavelength is, for example, 700 nm, and the fourth wavelength is, for example, 1000 nm. The third wavelength and the fourth wavelength are not limited to the above wavelengths. These wavelengths may be free of influence from an absorption wavelength band of oxyhemoglobin (not less than 520 nm nor more than 590 nm) and an absorption wavelength of $H_2O$ that is a solvent (1450 nm). Specifically, the third wavelength and the fourth wavelength may be a wavelength of not less than 600 nm nor more than 1350 nm, more preferably not less than 600 nm nor more than 1000 nm.

The normalization part 31 calculates (normalizes) the ratio of the intensity of the light at the fourth wavelength to the intensity of the light at the third wavelength by assuming that the intensity of the light at the third wavelength, which is emitted from the light source 1 and passed through the body fluid and detected by the detector 2 is, for example, 1.

The calculation part 32 calculates a degree of hemolysis in the body fluid on the basis of the intensity of the light at the fourth wavelength thus normalized and a calibration curve and a table previously obtained by using a body fluid having a known hemoglobin concentration and a known degree of hemolysis. Examples of the calibration curve include a regression equation of a degree of hemolysis by means of a monomial according to the hemoglobin concentration.

Alternatively, a fifth wavelength, which is different from the third wavelength or the fourth wavelength, may also be measured. An intensity of the light at the fifth wavelength may be normalized by the intensity of the light at the third wavelength. A degree of hemolysis can be obtained more accurately by obtaining the degree of hemolysis on the basis of the normalized intensity of the light at the fourth wavelength and the normalized intensity of the light at the fifth wavelength. In this case, the calculation part 32 calculates the degree of hemolysis in the body fluid on the basis of the normalized intensity of the light at the fourth wavelength and the normalized intensity of the light at the fifth wavelength, and the calibration curve and the table obtained by using the body fluid having the known hemoglobin concentration and the known degree of hemolysis. Examples of the calibration curve in this case include a regression equation of a degree of hemolysis by means of a polynomial according to the hemoglobin concentration.

The fifth wavelength may be free of influence from an absorption wavelength band of oxyhemoglobin (not less than 520 nm nor more than 590 nm) and an absorption wavelength (1450 nm) of $H_2O$ that is a solvent. Specifically, the fifth wavelength may be a wavelength of not less than 600 nm nor more than 1350 nm, more preferably not less than 600 nm nor more than 1000 nm.

The first wavelength and the third wavelength may be the same so that the first wavelength is usable as the third wavelength. Of course, these two wavelengths may not be the same.

The method by which the normalization part calculates the ratio of the intensity of the light at the second wavelength to that of the light at the first wavelength, or the ratio of the light at the fourth wavelength and the light at the fifth wavelength to the light at the third wavelength is not limited to the method described above. For example, the intensity of the light at the first wavelength or the third wavelength may be assumed to be a figure other than 1. The ratio may be obtained by other method.

The body fluid analysis device 100 may further include a determination part and a display part. The determination part determines a level of a degree of hemolysis by applying numerical values, such as a hemoglobin concentration, a hematocrit value, a concentration of blood in urine, to a predetermined numerical value range. The display part displays an analysis result outputted from the determination part and the calculation part 32.

The body fluid is not limited to urine but may be fluid obtainable from a living body, such as sweat, saliva and blood.

The above embodiment has been described as one example which is configured to analyze the urine inside the urinary catheter which is drawn outside the body by a balloon catheter, without being limited thereto. For example, the body fluid, such as blood in the living body, may be directly analyzed or other methods may be used. Alternatively, a body fluid that is extracted and stored in a container may be analyzed.

Other various modifications and combinations of the embodiments may be made without departing from the spirit and scope of the present invention.

EXAMPLES

The body fluid analysis device and the body fluid analysis method in the present invention are described in more detail below by exemplifying embodiments. However, the present invention is not limited to these embodiments.

Figure 2:
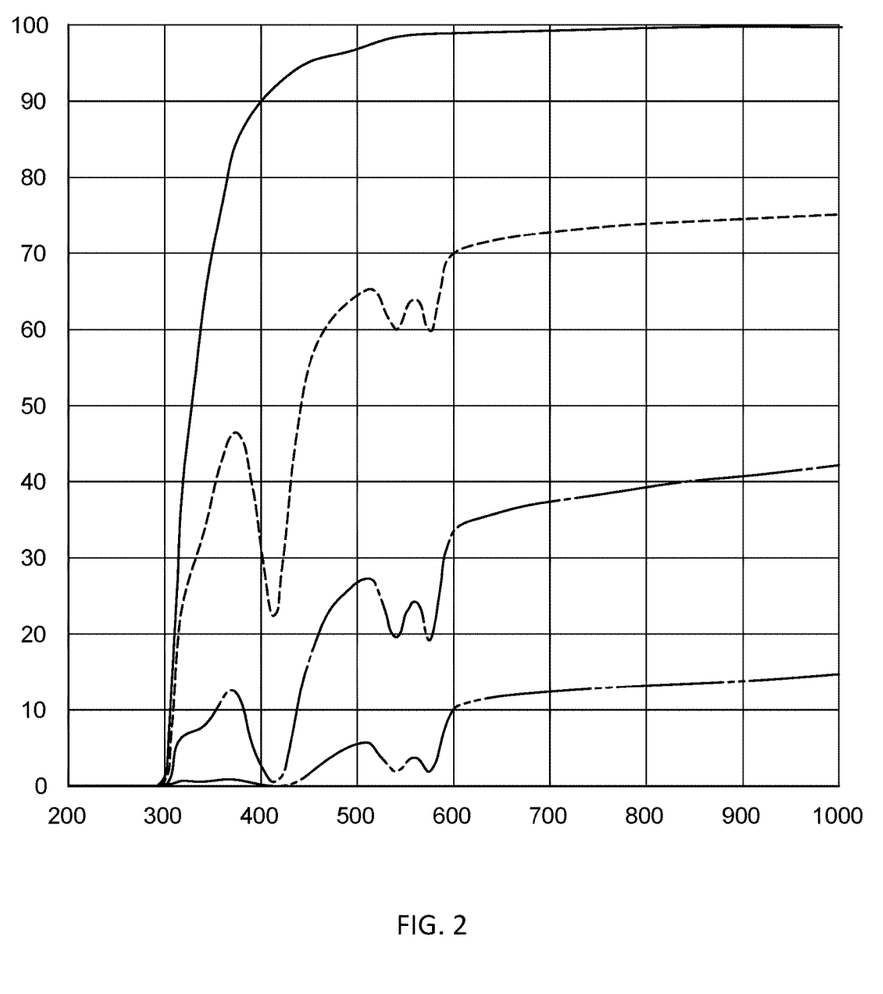
FIG. 2 is a graph indicating light intensities at individual wavelengths before normalization in urine in the absence of hemolysis according to an embodiment of the present invention.
Figure 3:
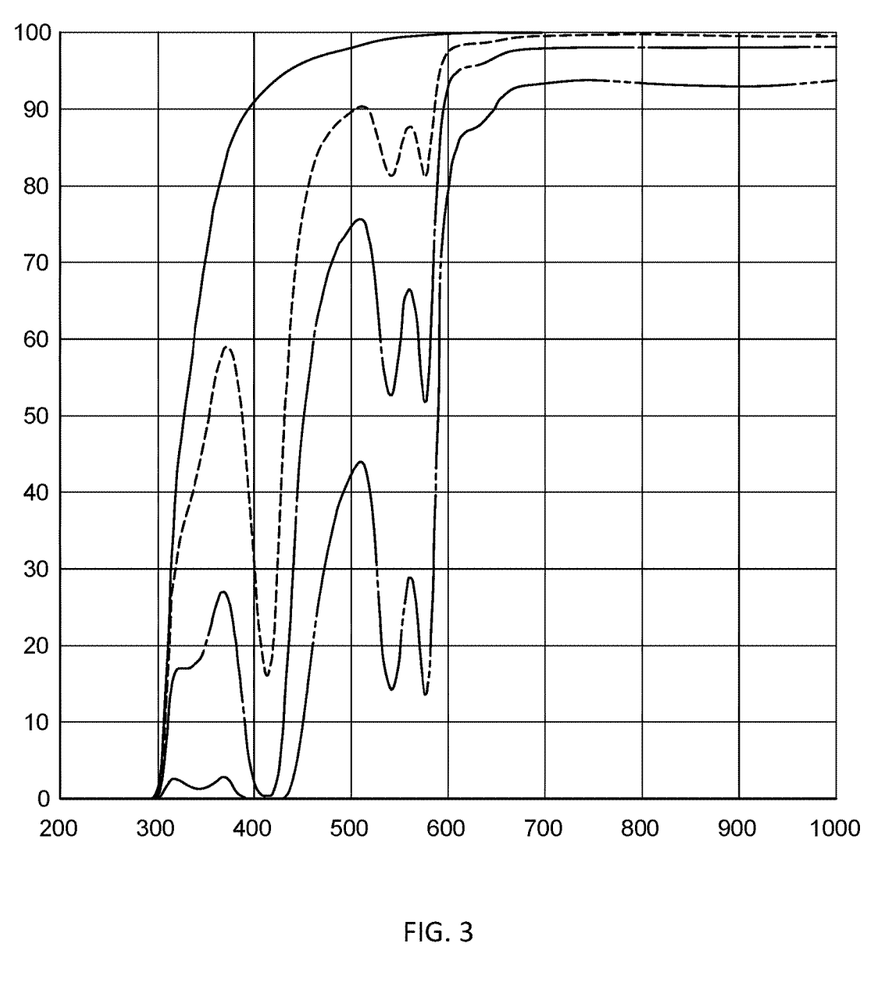
FIG. 3 is a graph indicating light intensities at individual wavelengths before normalization in urine in the presence of hemolysis according to an embodiment.

FIGS. 2 and 3 illustrate intensities of transmitted light at wavelengths of not less than 300 nm nor more than 1000 nm in the urine inside the urinary catheter as described above. In the graphs of FIGS. 2 to 5, a solid line indicates urine with a hemoglobin concentration regulated to 0.00 g/dL, a broken line indicates urine with a hemoglobin concentration regulated to 0.10 g/dL, a chain line indicates urine with a hemoglobin concentration regulated to 0.34 g/dL, and a long dashed double-dotted line indicates urine with a hemoglobin concentration regulated to 1.02 g/dL.

FIG. 2 is the graph of urine that includes blood in the complete absence of hemolysis.

FIG. 3 is the graph of urine including blood subjected to complete hemolysis.

A comparison between FIGS. 2 and 3 shows that the intensities of light transmitted at individual wavelengths differ considerably depending on the presence or absence of hemolysis.

Hence, the present inventor has found that the hemoglobin concentration of the body fluid cannot be calculated accurately only by detecting a wavelength around 850 nm.

The present inventor has similarly found that the hemoglobin concentration of the body fluid cannot be calculated accurately only by detecting a wavelength of not less than 520 nm nor more than 590 nm which is the absorption band of oxyhemoglobin.

As a result of earnest consideration for solving the above problems, the present inventor conceived an idea of calculating and normalizing a ratio of an intensity of light at a second wavelength when the intensity of light at a first wavelength of 850 nm is set to 1 in the above graphs. Graphs of FIGS. 4 and 5 show the results of the normalization of the above individual graphs.

Figure 4:
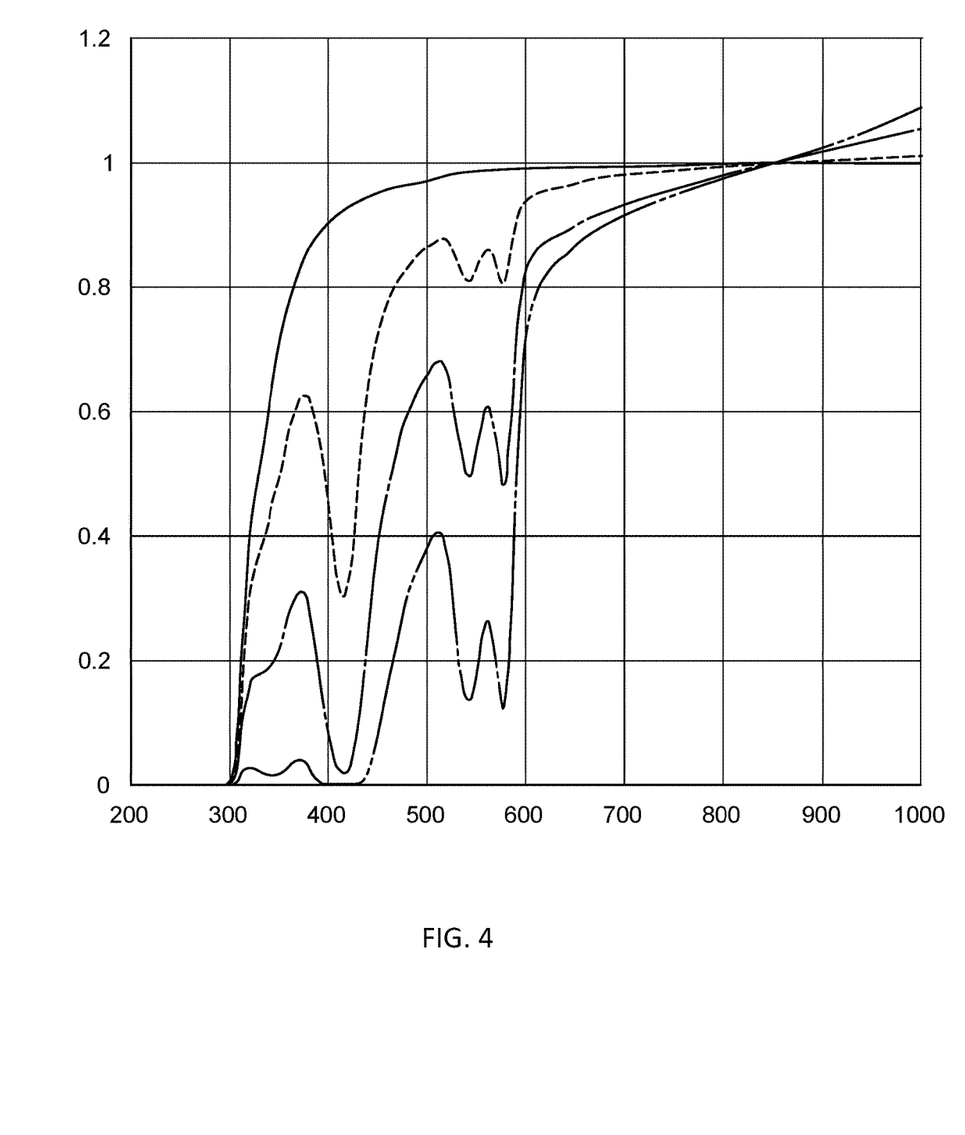
FIG. 4 is a graph indicating light intensities at individual wavelengths after normalization in urine in the complete absence of hemolysis according to an embodiment.

FIG. 4 is the graph obtained by normalizing the graph of FIG. 2. FIG. 5 is the graph obtained by normalizing the graph of FIG. 3.

Figure 5:
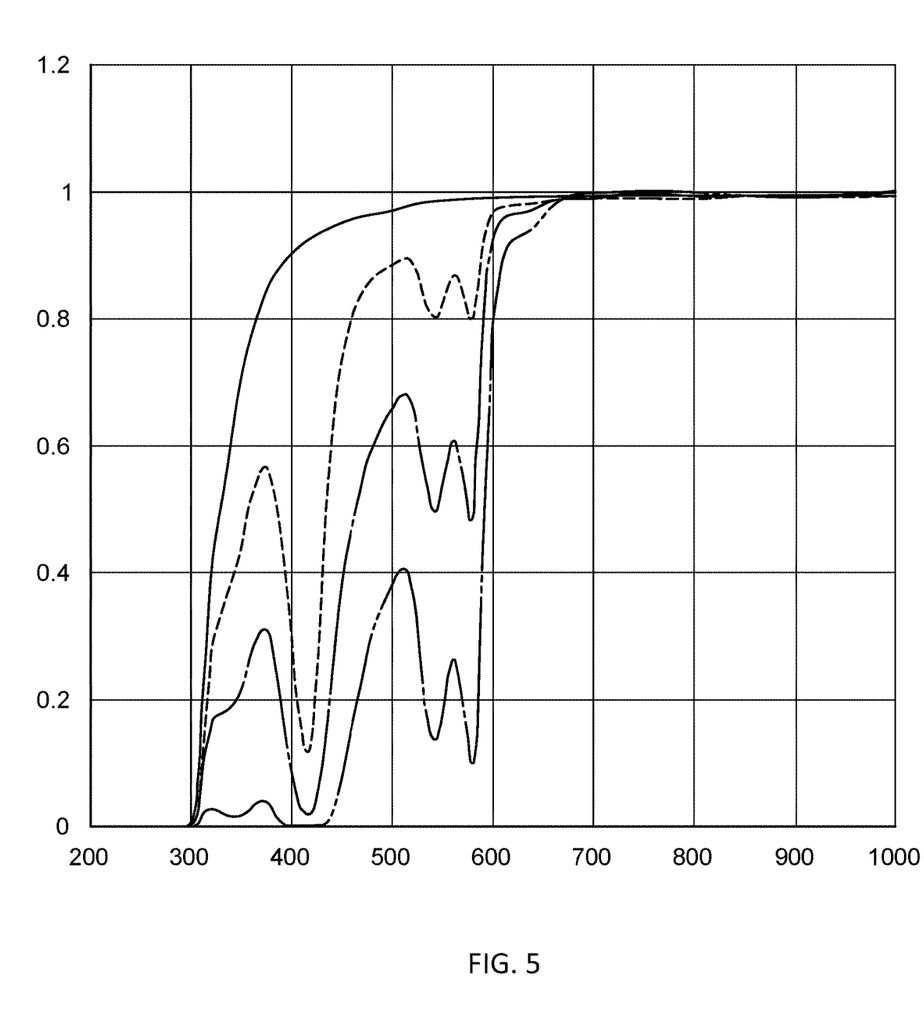
FIG. 5 is a graph indicating light intensities at individual wavelengths after normalization in urine in the presence of complete hemolysis according to an embodiment.

As can be seen from FIG. 3, the following has been found from a comparison between FIGS. 4 and 5. That is, by normalizing through setting the intensity of light at a first wavelength of 850 nm to 1, the same behavior appears in FIG. 4 in the absence of hemolysis and FIG. 5 in the presence of hemolysis, as indicated by a change in a ratio of the intensity of light at the second wavelength of 560 nm to the intensity of the light at the first wavelength with respect to a hemoglobin concentration.

The following conclusions have been made from these results. A hemoglobin concentration can be calculated more accurately than conventionally on the basis of the ratio of the intensity of light at the second wavelength to the intensity of light at the first wavelength, and creating a calibration curve or a table using urine having a known hemoglobin concentration. Similarly, the hematocrit value converted from the hemoglobin concentration can also be calculated accurately.

A change in intensity of transmitted light relative to the hemoglobin concentration becomes large when the second wavelength is around 550-560 nm, regardless of the degree of hemolysis. Therefore, the hemoglobin concentration and hematocrit value can be calculated more accurately by employing the above band as the second wavelength.

The present invention was first accomplished based on the findings by the present inventor that, by calculating a ratio of the intensity of light at the second wavelength to the intensity of light at the first wavelength, the hemoglobin concentration can be calculated accurately on the basis of the ratio as described above.

The present inventor has also found that a comparison between FIGS. 4 and 5 shows a difference in slope of graph in a wavelength range of not less than 600 nm nor more than 1000 nm.

Because the conditions in FIGS. 4 and 5 differ only in the presence or absence of hemolysis, it can be concluded that the difference in the slope of the graph is due to the presence or absence of hemolysis.

In another example, 850 nm is selected as a third wavelength, and 1000 nm is selected as a fourth wavelength. The intensity of light transmitted through urine at each of these wavelengths is detected. Assuming that the intensity of the transmitted light at the third wavelength is 1, a ratio of the intensity of the light at the fourth wavelength to the intensity of the light at the third wavelength is calculated. A degree of hemolysis in a body fluid, such as urine, can be calculated by calculating a slope of graph from the ratio.

In an additional example, 850 nm is selected as a third wavelength, 700 nm is selected as a fourth wavelength and 1000 nm is selected as a fifth wavelength. The intensity of light transmitted through urine at each of these wavelengths is detected. Assuming that the intensity of the transmitted light at the third wavelength is 1, a ratio of the intensity of each of the light at the fourth wavelength and the light at the fifth wavelength to the intensity of the light at the third wavelength is calculated. A degree of hemolysis of a body fluid, such as urine, can be calculated more accurately by calculating a slope of graph in a range of 700-850 nm and a slope of graph in a range of 850-1000 nm from these ratios.

The data indicated herein is related to embodiments described in the present invention and has been confirmed in experiments. Similarly to the described embodiments, a hemoglobin concentration, a hematocrit value and a degree of hemolysis can be calculated accurately even in cases where the solution including blood is a saline solution, and the first wavelength is changed to a different wavelength, such as 600 nm, 650 nm, 700 nm, 750 nm, 800 nm, 900 nm, and 950 nm. Particularly, it has been found that if the first wavelength is set to 650 nm and the second wavelength is set to 550 nm, the hemoglobin concentration can be calculated with minimal influence from hemolysis.

INDUSTRIAL APPLICABILITY

With the present invention, it is possible to provide a body fluid analysis device capable of accurately measuring the degree of occult blood in a body fluid, such as urine, even in the presence of hemolysis.

What is claimed is:

1. A body fluid analysis device comprising:
a light source configured to emit light at a first wavelength and light at a second wavelength different from the first wavelength to irradiate a body fluid;
a detector configured to receive the light emitted from the light source and transmitted through the body fluid or reflected by the body fluid, and configured to detect an intensity of the light emitted at the first wavelength and an intensity of the light emitted at the second wavelength; and
a processor configured to implement an information processing circuit to:
calculate a ratio of the intensity of the light emitted at the second wavelength to the intensity of the light emitted at the first wavelength, and
calculate a concentration of a predetermined component included in the body fluid on a basis of the ratio, wherein the first wavelength is not less than 600 nm nor more than 1350 nm, and the second wavelength is not less than 300 nm nor more than 600 nm.

2. The body fluid analysis device according to claim 1, wherein the body fluid is urine and the predetermined component is hemoglobin included in blood.

3. The body fluid analysis device according to claim 1, wherein the body fluid is urine and the predetermined component is blood cells included in blood.

4. The body fluid analysis device according to claim 1, wherein the information processing circuit is configured to calculate a hematocrit value from a calculated concentration of hemoglobin.

5. A body fluid analysis device comprising:
- a light source configured to emit light at a first wavelength and light at a second wavelength different from the first wavelength to irradiate a body fluid;
- a detector configured to receive the light emitted from the light source and transmitted through the body fluid or reflected by the body fluid, and configured to detect an intensity of the light emitted at the first wavelength and an intensity of the light emitted at the second wavelength; and
- a processor configured to implement an information processing circuit to:
  - calculate a ratio of the intensity of the light emitted at the second wavelength to the intensity of the light emitted at the first wavelength, and
  - calculate a degree of hemolysis in the body fluid on a basis of the ratio, wherein the first wavelength and the second wavelength are not less than 600 nm nor more than 1350 nm.

6. A body fluid analysis method comprising:
- emitting light at a first wavelength and light at a second wavelength different from the first wavelength to irradiate a body fluid;
- receiving the light emitted at the first wavelength and the light emitted at the second wavelength, both of which are transmitted through the body fluid or reflected by the body fluid;
- detecting an intensity of the light emitted at the first wavelength and an intensity of the light emitted at the second wavelength;
- calculating a ratio of the intensity of the light emitted at the second wavelength to the intensity of the light emitted at the first wavelength; and
- calculating a concentration of a predetermined component included in the body fluid on a basis of the ratio, wherein the first wavelength is not less than 600 nm nor more than 1350 nm, and the second wavelength is not less than 300 nm nor more than 600 nm.

7. A body fluid analysis method comprising:
- emitting light at a first wavelength and light at a second wavelength different from the first wavelength to irradiate a body fluid;
- receiving the light emitted at the first wavelength and the light emitted at the second wavelength, both of which are transmitted through the body fluid or reflected by the body fluid;
- detecting an intensity of the light emitted at the first wavelength and an intensity of the light emitted at the second wavelength;
- calculating a ratio of the detected intensity of the light emitted at the second wavelength to the detected intensity of the light emitted at the first wavelength; and
- calculating a degree of hemolysis in the body fluid on a basis of the ratio, wherein the first wavelength and the second wavelength are not less than 600 nm nor more than 1350 nm.

8. A body fluid analysis device comprising:
- a light source configured to emit light at a first wavelength and light at a second wavelength different from the first wavelength to irradiate a body fluid;
- a detector configured to receive the light emitted from the light source and transmitted through the body fluid or reflected by the body fluid, and configured to detect an intensity of the light emitted at the first wavelength and an intensity of the light emitted at the second wavelength; and
- a processor configured to implement an information processing circuit to:
  - calculate a ratio of the intensity of the light emitted at the second wavelength to the intensity of the light emitted at the first wavelength,
  - calculate a concentration of a predetermined component included in the body fluid on a basis of the ratio, and
  - calculate a hematocrit value from a calculated concentration of hemoglobin.

* * * * *